(12) United States Patent
Bradshaw et al.

(10) Patent No.: US 8,945,525 B2
(45) Date of Patent: Feb. 3, 2015

(54) COMFORTABLE, LONG-WEARING, TRANSFER-RESISTANT COLORED COSMETIC COMPOSITIONS HAVING HIGH GLOSS AND A NON-TACKY FEEL

(75) Inventors: Kimberly Bradshaw, Monmouth Junction, NJ (US); Hy Si Bui, Piscataway, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/981,882

(22) Filed: Dec. 30, 2010

(65) Prior Publication Data

US 2012/0171138 A1 Jul. 5, 2012

(51) Int. Cl.
*A61K 8/00* (2006.01)
*A61K 8/31* (2006.01)
*A61K 8/891* (2006.01)
*A61Q 1/06* (2006.01)
*A61K 8/898* (2006.01)

(52) U.S. Cl.
CPC . *A61K 8/31* (2013.01); *A61K 8/891* (2013.01); *A61Q 1/06* (2013.01); *A61K 8/898* (2013.01); *A61K 2800/594* (2013.01); *A61K 2800/31* (2013.01)
USPC .......................................... 424/70.1; 424/401

(58) Field of Classification Search
None
See application file for complete search history.

(56) References Cited

U.S. PATENT DOCUMENTS

| | | | |
|---|---|---|---|
| 5,874,069 A | 2/1999 | Mendolia et al. | |
| 5,919,441 A | 7/1999 | Mendolia et al. | |
| 5,981,680 A | 11/1999 | Petroff et al. | |
| 6,051,216 A | 4/2000 | Barr et al. | |
| 6,964,773 B1 | 11/2005 | Morrison | |
| 2004/0115154 A1 | 6/2004 | Yu | |
| 2006/0110347 A1* | 5/2006 | Lu et al. ....................... | 424/70.1 |
| 2007/0093619 A1 | 4/2007 | Bui et al. | |

FOREIGN PATENT DOCUMENTS

EP 1 854 450 11/2007

OTHER PUBLICATIONS

U.S. Appl. No. 12/981,867, filed Dec. 30, 2010, Bui et al.
U.S. Appl. No. 12/982,108, filed Dec. 30, 2010, Bui et al.
U.S. Appl. No. 12/982,061, filed Dec. 30, 2010, Bradshaw et al.
U.S. Appl. No. 12/981,839, filed Dec. 30, 2010, Bradshaw et al.
U.S. Appl. No. 12/981,882, filed Dec. 30, 2010, Bradshaw et al.
Written Opinion and International Search Report as received in the corresponding International Application No. PCT/EP2011/074019 dated Feb. 21, 2014.
Communication as received in the corresponding European Patent Application No. 11808870.7-1458 / 2729218 dated Apr. 22, 2014.

* cited by examiner

*Primary Examiner* — Lezah Roberts
*Assistant Examiner* — Nannette Hollowman
(74) *Attorney, Agent, or Firm* — Oblon, Spivak, McClelland, Maier & Neustadt, L.L.P.

(57) ABSTRACT

The present invention is directed to an anhydrous glossy composition which is long wearing and transfer resistant, while at the same time providing superior comfort, non-tacky feel and cushioning, the composition containing (a) at least one siloxysilicate resin; (b) at least one polyorganosiloxane-containing polymer; (c) at least one volatile solvent; (d) at least one non-volatile solvent having more than one phenyl group; and (e) optionally, at least one colorant; and wherein the ratio by weight of (b) to (a) is greater than or equal to 1.

20 Claims, No Drawings

COMFORTABLE, LONG-WEARING, TRANSFER-RESISTANT COLORED COSMETIC COMPOSITIONS HAVING HIGH GLOSS AND A NON-TACKY FEEL

BACKGROUND OF THE INVENTION

Cosmetic compositions used to make up or enhance the appearance of a user's skin are oftentimes required to be able to impart various properties such as gloss, long wear and transfer resistance. However, the formulation of cosmetic products that can deliver all these properties at the same time can pose some challenges. For example, cosmetic compositions using traditional ingredients known to impart gloss, such as oils, have very poor transfer resistance and wear properties. In order to overcome these problems, film forming resins such as silicone film forming resins are generally employed to improve the transfer resistance and wear of cosmetic compositions. While the use of silicone film forming resins in cosmetics is popular, one drawback associated with their use is that they tend to be brittle and flake off. This phenomenon results in the need to use a plasticizer, in combination with the resin, in order to render the resultant film more flexible and, hence, less susceptible to flake off and poor transfer resistance. Moreover, the resultant films formed by the resins are not glossy, are uncomfortable on human skin and, at times, have a tacky feel.

Therefore, it is an object of the present invention to provide a method and composition for making up skin in a manner which delivers a combination of high gloss, transfer resistance and long wear, as well as superior comfort and a non-tacky feel.

BRIEF SUMMARY OF THE INVENTION

According to one embodiment of the present invention, there is provided an anhydrous glossy composition which is long wearing and transfer resistant, while at the same time providing superior comfort, non-tacky feel and cushioning, the composition containing:
  (a) at least one siloxysilicate resin;
  (b) at least one polyorganosiloxane-containing polymer;
  (c) at least one volatile solvent;
  (d) at least one non-volatile solvent having more than one phenyl group; and
  (e) optionally, at least one colorant;
  and wherein the ratio by weight of (b) to (a) is greater than or equal to 1.

According to another aspect of the present invention, there is provided a method of making up skin involving applying onto the skin the above-disclosed composition.

It has been surprisingly discovered that the above-described glossy cosmetic composition provides superior non-tacky feel, transfer resistance, long wear and comfort when applied onto a keratinous substrate.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Substituted" as used herein, means comprising at least one substituent. Non-limiting examples of substituents include atoms, such as oxygen atoms and nitrogen atoms, as well as functional groups, such as amine groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The compositions and methods of the present invention can comprise, consist of, or consist essentially of the essential elements and limitations of the invention described herein, as well as any additional or optional ingredients, components, or limitations described herein or otherwise useful.

The cosmetic compositions of the present invention further comprise at least one siloxysilicate. One non-limiting example of a siloxysilicate in accordance with the present invention is trimethylsiloxysilicate, which may be represented by the following formula:

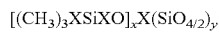

[(CH$_3$)$_3$XSiXO]$_x$X(SiO$_{4/2}$)$_y$ wherein x and y may, for example, range from 50 to 80. Such siloxysilicates are commercially available from General Electric and Dow Corning under the tradename Resin MQ®.

The at least one siloxysilicate is generally present in the cosmetic composition of the present invention in an amount ranging from about 5% to about 30% by weight; such as from about 10% to about 25% by weight; such as from about 15% to about 20% by weight, all weights being based on the weight of the composition as a whole.

The glossy cosmetic compositions of the present invention also comprise at least one polyorganosiloxane-containing polymer. The polyorganosiloxane-containing polymer useful herein is a polymer (homopolymer or copolymer) having at least one moiety which contains: at least one polyorganosiloxane group consisting of 1 to about 1000 organosiloxane units in the chain of the moiety or in the form of a graft, and at least two groups capable of establishing hydrogen interactions.

The polyorganosiloxane-containing polymers may comprise at least one moiety corresponding to formula (I):

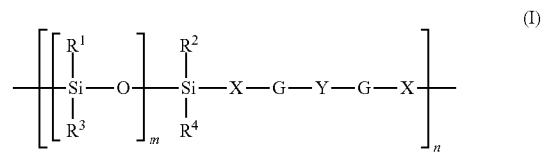

in which:
1) $R^1$, $R^2$, $R^3$ and $R^4$, which may be identical or different, represent a group chosen from:
   (a) linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms,
   (b) $C_6$ to $C_{10}$ aryl groups, optionally substituted with one or more $C_1$ to $C_4$ alkyl groups,
   (c) polyorganosiloxane chains possibly containing one or more oxygen, sulphur and/or nitrogen atoms;
2) X, which may be identical or different, represents a linear or branched $C_1$ to $C_{30}$ alkylenediyl group, possibly containing in its chain one or more oxygen and/or nitrogen atoms;
3) Y is a saturated or unsaturated, $C_1$ to $C_{50}$ linear or branched divalent alkylene, arylene, cycloalkylene, alkylarylene or arylalkylene group, optionally comprising one or more oxygen, sulphur and/or nitrogen atoms, and/or optionally substituted with one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with one to three $C_1$ to $C_3$ alkyl, $C_1$ to $C_3$ hydroxyalkyl, and $C_1$ to $C_6$ aminoalkyl groups;
4) G, which may be identical or different, represents a group chosen from ester, amide, sulphonamide, carbamate, thiocarbamate, urea, thiourea groups, and combinations thereof;
5) m is an integer ranging from 1 to 1,000, preferably from 1 to 700 and more preferably from 6 to 200; and
6) n is an integer ranging from 2 to 500 and preferably from 2 to 200.

The polyorganosiloxane-containing polymers may also comprise at least one moiety corresponding to formula (II):

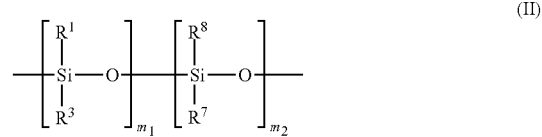

in which
$R^1$ and R, which may be identical or different, are as defined above for formula (I), $R^7$ represents a group as defined above for $R^1$ and $R^3$, or represents a group of formula $-X-G-R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula $-X-G-R^9$ in which X, G and $R^9$ are as defined above, $m_1$ is an integer ranging from 1 to 998, and $m_2$ is an integer ranging from 2 to 500.

According to another embodiment, it is also possible to use a copolymer comprising several different moieties of formula (I), and/or several different moieties of formula (II), that is to say a polymer in which at least one of the groups $R^1$, $R^2$, $R^3$, $R^4$, X, G, Y, m and n is different in one of the moieties.

It is also possible to use a copolymer comprising at least one moiety of formula (I) and at least one moiety of formula (II), the moieties of formula (I) and the moieties of formula (II) possibly being identical to, or different from, each other. These copolymers may be block copolymers or grafted copolymers.

Additional polyorganosiloxane-containing polymers which may be used in the composition of the invention include those described in documents U.S. Pat. Nos. 5,874,069, 5,919,441, 6,051,216, and 5,981,680, the entire contents of which are hereby incorporated by reference.

A preferred polyorganosiloxane-containing polymer for use in the present invention will have at least one moiety chosen from formula (III):

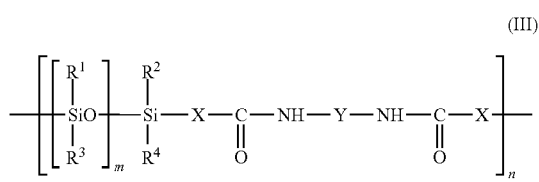

and formula (IV)

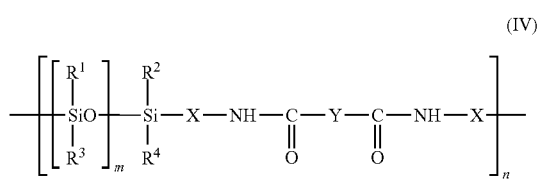

in which:

(a) $R^1$, $R^2$, $R^3$ and $R^4$ are the same or different and may be selected from the group consisting of methyl, ethyl, propyl, isopropyl, a siloxane chain, and phenyl;

(b) X is a linear or branched chain alkylene having 1-30 carbons;

(c) Y is selected from the group consisting of linear or branched chain alkylenes having 1-40 carbons;

(d) m is a number between 1 and 700;

(e) n is a number between 1 and 500.

Particularly preferred polyorganosiloxane-containing polymers useful herein are commercially available from Dow Corning under the tradenames DC 8178® and DC 8179®, which are known under the INCI denomination of Nylon-611/Dimethicone Copolymer.

The at least one polyorganosiloxane-containing polymer is generally present in the cosmetic composition of the present invention in an amount ranging from about 5% to about 40% by weight; such as from about 10% to about 35% by weight; such as from about 15% to about 30% by weight, all weights being based on the weight of the composition as a whole.

According to the present invention, the ratio by weight of the at least one polyorganosiloxane-containing polymer to the at least one siloxysilicate is greater than or equal to 1.0, such as from about 1.5:1.0, from about 2.0:1.0, from about 2.5:1, and from about 3.0:1.0.

The composition of the invention also contains at least one volatile solvent.

The expression "volatile solvent" means any non-aqueous medium capable of evaporating on contact with the skin or the lips in less than one hour at room temperature and atmospheric pressure.

Examples of suitable volatile solvents include volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
|---|---|
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile solvent may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |

TABLE 2-continued

| Compound | Flash Point (° C.) | Viscosity (cSt) |
|---|---|---|
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

The at least one volatile solvent is generally present in the cosmetic composition of the present invention in an amount ranging from about 5% to about 50% by weight; such as from about 10% to about 35% by weight; such as from about 15% to about 25% by weight, all weights being based on the weight of the composition as a whole.

According to the present invention, the non-volatile solvent having more than one phenyl group is preferably a non-volatile silicone having more than one phenyl group, such a non-volatile silicone having two phenyl groups, a non-volatile silicone having three phenyl groups, a non-volatile silicone having four phenyl groups, a non-volatile silicone having five phenyl groups, and the like. A particularly preferred non-volatile silicone having more than one phenyl group is pentaphenyldimethicone, also known as trimethyl pentaphenyl trisiloxane, commercially available from Dow Corning under the tradename DC555®.

Other preferred non-volatile silicones are phenyl trimethicone compounds and polyphenyl trimethicone compounds having molecular weights of at least 3000 Da and/or viscosities of at least 100 cSt such as phenyl trimethicone which is commercially available from Evonik Goldschmidt under the tradenames ABIL AV 350 (300±30 cSt) and ABIL AV 1000 (925-1075 cSt) and also commercially available from Dow Corning under the tradename of DOW CORNING DC1-0648 (at least 5000 cSt), trimethylsiloxyphenyl dimethicone which is commercially available from Wacker under the tradename WACKER-BELSIL PDM 1000 (925-1075 cSt), and diphenylsiloxy phenyl trimethicone which is commercially available from Facconier.

The at least one non-volatile solvent is generally present in the cosmetic composition of the present invention in an amount ranging from about 5% to about 50% by weight; such as from about 10% to about 40% by weight; such as from about 15% to about 30% by weight, all weights being based on the weight of the composition as a whole.

The cosmetic compositions of the present invention may also contain at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation. However, one preferred amount of colorant for use in the present invention is from about 0.5% to about 7.5%, based on the weight of the composition.

Additives/Auxiliary Agents

The compositions of the present invention may further comprise at least one cosmetically or dermatologically acceptable additive such as a thickener, a film former, a plasticizer, an antioxidant, an essential oil, a preserving agent, a fragrance, a filler, a pasty fatty substance, a waxy fatty substance, a neutralizing agent, and a polymer, and cosmetically active agents and/or dermatological active agents such as, for example, emollients, moisturizers, vitamins, essential fatty acids and medicaments.

Fillers that may be used in the compositions of the invention include, for example, silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo by the company National. Starch; silicone resin microbeads such as those sold under the name Tospearl by the company Toshiba Silicone; clays (bentone, laponite, saponite, etc.); and mixtures thereof.

The fillers may be present in the composition of the invention in an amount ranging from about 0.1% to about 50% by weight, such as from 0.5% to about 30% by weight, and such as from about 1% to about 20% by weight, all weights based on the weight of the composition as a whole.

It has been surprisingly discovered that by combining in a composition, at least one siloxysilicate resin and at least one polyorganosiloxane-containing polymer, in a ratio where the weight of the polyorganosiloxane-containing polymer to the weight of the siloxysilicate resin is greater than or equal to 1, at least one volatile solvent and at least one non-volatile solvent such as trimethyl pentaphenyl trisiloxane (DC555®), a glossy cosmetic composition with excellent wear and transfer-resistance properties is achieved.

According to a preferred embodiment of the present invention, compositions having improved cosmetic properties such as, for example, improved waterproof characteristics, improved feel upon application (for example, texture, reduced drag or tackiness), increased anti-smudging properties, and shine/color characteristics are also provided.

According to other embodiments of the present invention, methods of improving the anti-smudging, waterproof, glossiness, transfer-resistance and/or long wear properties of a composition, comprising adding to the composition, at least one siloxysilicate resin, at least one polyorganosiloxane-containing polymer wherein the ratio by weight of the polyorganosiloxane-containing polymer to the weight of the siloxysilicate resin is greater than or equal to 1, at least one volatile solvent and at least one non-volatile solvent such as DC555® are provided.

The present invention will be better understood from the examples which follow, all of which are intended for illustrative purposes only.

EXAMPLES

A lip composition in accordance with the present invention was formulated. The ingredients employed are found in Table 1, below.

| Ingredient | % by weight |
| --- | --- |
| DC555 ® SILICONE FLUID | 17.0 |
| MQ ® resin | 12.0 |
| isododecane | 18.9 |
| Bentone gel | 25.0 |
| Lauroyl lysine | 1.5 |
| Nylon-611/Dimethicone Copolymer | 18.0 |
| pigments | 7.5 |
| fragrance | 1.0 |

TABLE 2

COMPARATIVE DATA
MQ ® + PSPA + DC555 ® + IDD

| | PSPA:MQ ® | | | |
| --- | --- | --- | --- | --- |
| | 1:1.5 | 1:3 | 1.5:1 | 3:1 |
| MQ ® RESIN/TRIMETHYLSILOXYSILICATE/SR 1000 ® | 18 | 22.56 | 12 | 7.52 |
| PSPA/NYLON-611/DIMETHICONE COPOLYMER/DOW CORNING 2-8179 ® GELLANT | 12 | 7.52 | 18 | 22.56 |
| TRIMETHYL PENTAPHENYL TRISILOXANE/TRIMETHYL PENTAPHENYL TRISILOXANE/DOW CORNING PH-1555 HRI COSMETIC FLUID (DC555 ® silicone fluid) | 17 | 17 | 17 | 17 |
| ISODODECANE/ISODODECANE | 18.9 | 18.82 | 18.9 | 18.82 |
| BENTONE GEL/DISTEARDIMONIUM HECTORITE (and) PROPYLENE CARBONATE/BENTONE GEL ISD V | 25 | 25 | 25 | 25 |
| LAUROYL LYSINE/AMIHOPE LL | 1.5 | 1.5 | 1.5 | 1.5 |
| IRON OXIDES (CI 77499)/SICOVIT NOIR 85 E 172 | 0.63 | 0.63 | 0.63 | 0.63 |
| YELLOW 6 LAKE ( CI 15985) SUNCROMA FD&C YELLOW 6 AL LAKE C70-5270 | 1.45 | 1.45 | 1.45 | 1.45 |
| RED 7( CI 15850)/UNIPURE RED LC 3079 OR | 1.24 | 1.24 | 1.24 | 1.24 |
| RED 28 LAKE (CI 45410)/SUNCROMA D&C RED 28 AL LAKE C14-6623 | 0.35 | 0.35 | 0.35 | 0.35 |
| MICA (CI: 77019) | 3.83 | 3.83 | 3.83 | 3.83 |
| FRAGRANCE/PARFUM/ | 0.1 | 0.1 | 0.1 | 0.1 |
| NON-TRANSFER EVALUATION | MODERATE | MODERATE | GOOD | GOOD |
| WEAR EVALUATION 0 = GOOD WEAR, 5 = NO WEAR | | | | |
| WEAR EVALUATION WITH OLIVE OIL | 1 | 1 | 1 | 1 |
| WEAR EVALUATION WITH SQUALANE | 1 | 1 | 1 | 1 |

The compositions above were tested for transfer-resistance according to the "kiss test" as described above. They were also tested for wear using a test involving the following steps:
applying the composition on the surface of an elastic flat stretch band at 30 degrees Celsius,
allowing the composition to form a film on the band,
placing a drop of olive oil or squalane onto the film,
letting the oil dry for 5 minutes at room temperature, and
then rubbing a cotton tip onto the dried composition.

The degree of wear was evaluated by noting how much of the film was removed.

TABLE 3

| | PSPA:MQ® 1.5:1 | | PSPA:MQ® 3:1 | |
|---|---|---|---|---|
| MQ® RESIN/TRIMETHYLSTLOXYSILICATE/ SR 1000 | 12 | 12 | 7.52 | 7.52 |
| PSPA/NYLON-611/DIMETHICONE COPOLYMER/DOW CORNING 2-8179® GELLANT | 18 | 18 | 22.56 | 22.56 |
| TRIMETHYL PENTAPHENYL TRISILOXANE/TRIMETHYL PENTAPHENYL TRISILOXANE/ DOW CORNING PH-1555 HRI COSMETIC FLUID (DC555® silicone fluid) | 17 | 0 | 17 | 0 |
| DIMETHICONE/XIAMETER PMX-200 SILICONE FLUID 350CS | 0 | 17 | 0 | 17 |
| ISODODECANE/ISODODECANE | 18.9 | 18.9 | 18.82 | 18.82 |
| BENTONE GEL/ DISTEARDIMONIUM HECTORITE (and) PROPYLENE CARBONATE/ BENTONE GEL ISD V | 25 | 25 | 25 | 25 |
| LAUROYL LYSINE/AMIHOPE LL | 1.5 | 1.5 | 1.5 | 1.5 |
| IRON OXIDES (CI 77499)/ SICOVIT NOIR 85 E 172 | 0.63 | 0.63 | 0.63 | 0.63 |
| YELLOW 6 LAKE ( CI 15985) SUNCROMA FD&C YELLOW 6 AL LAKE C70-5270 | 1.45 | 1.45 | 1.45 | 1.45 |
| RED 7( CI 15850)/UNIPURE RED LC 3079 OR | 1.24 | 1.24 | 1.24 | 1.24 |
| RED 28 LAKE (CI 45410)/ SUNCROMA D&C RED 28 AL LAKE C14-6623 | 0.35 | 0.35 | 0.35 | 0.35 |
| MICA (CI: 77019) | 3.83 | 3.83 | 3.83 | 3.83 |
| FRAGRANCE/PARFUM/ | 0.1 | 0.1 | 0.1 | 0.1 |
| NON-TRANSFER EVALUATION | GOOD | MODERATE | GOOD | MODERATE |
| WEAR EVALUATION 0 = GOOD WEAR, 5 = NO WEAR | | | | |
| WEAR EVALUATION WITH OLIVE OIL | 1 | 4 | 1 | 5 |
| WEAR EVALUATION WITH SQUALANE | 1 | 3 | 1 | 5 |

The same transfer-resistance and wear tests as described above were used.

It was surprisingly discovered that in the presence of DC555® silicone fluid (non volatile solvent having more than one phenyl group), the non-transfer and wear properties of the composition were much better than without it.

Procedures:
Procedure:
Phase A:

17% of DC555® was weighed out and added to a beaker. Then 17% of MQ® resin and 1.57% of Isododecane was weighed out and added to the beaker and the three were mixed using a propeller at about 350 rpm until the MQ® resin was completely dissolved in the DC555® and isododecane. Next 1.5% of lauroyl lysine and the pigments were weighed out and added to the beaker and mixed until the Lauroyl Lysine was dissolved and the pigments were wet. Next 25% of Bentone Gel was weighed out and added to the beaker and mixed until a smooth creamy texture was observed. The above mixture was then transferred to the disconti mill and ground until the pigments were completely dispersed.

Phase B:

In a separate beaker, 17.33% of isododecane, 18.00% of PSPA were weighed out and added to the beaker and allowed to heat at around 90 C until the PSPA was fully dispersed. The temperature source was then turned off and the batch was allowed to cool. The above Phase A was then added to phase B and the mixing was continued. When the batch reached around 65 C, pearls and fragrance were then added. The batch was then dropped at around 60 C. The batch was weighed to check for weight loss. Any weight loss was offset by adding isododecane.

The complete process was closely monitored and performed under closed kettle conditions to reduce the loss of isododecane.

What is claimed is:

1. An anhydrous glossy composition comprising:
   (a) at least one siloxysilicate resin;
   (b) at least one polyorganosiloxane-containing polymer;
   (c) at least one volatile solvent in an amount of about 5% to about 50% based on the total weight of the composition;
   (d) at least one non-volatile solvent having more than one phenyl group; and
   (e) optionally, at least one colorant; and wherein the ratio by weight of (b) to (a) is greater than or equal to 1.

2. The composition of claim 1 wherein (a) is trimethylsiloxysilicate.

3. The composition of claim 1 wherein (a) is present in the composition in an amount of from about 5 to about 30% by weight, based on the weight of the composition.

4. The composition of claim 1 wherein (b) is nylon-611/dimethicone copolymer.

5. The composition of claim 1 wherein (b) is present in the composition in an amount of from about 5 to about 40% by weight, based on the weight of the composition.

6. The composition of claim 1 wherein (d) is trimethyl pentaphenyl trisiloxane.

7. The composition of claim 1 wherein (d) is present in the composition in an amount of from about 5 to about 50% by weight, based on the weight of the composition.

8. The composition of claim 1 wherein the ratio by weight of (b) to (a) ranges from between about 1.5 to about 3.0.

9. A method of making up a keratinous substrate comprising applying onto the keratinous substrate an anhydrous glossy composition containing:
   (a) at least one siloxysilicate resin;
   (b) at least one polyorganosiloxane-containing polymer;
   (c) at least one volatile solvent in an amount of about 5% to about 50% based on the total weight of the composition;
   (d) at least one non-volatile solvent; and
   (e) optionally, at least one colorant; and
wherein the ratio by weight of (b) to (a) is greater than or equal to 1.

10. The method of claim 9 wherein (a) is trimethylsiloxysilicate.

11. The method of claim 9 wherein (a) is present in the composition in an amount of from about 5 to about 30% by weight, based on the weight of the composition.

12. The method of claim 9 wherein (b) is nylon-611/dimethicone copolymer.

13. The method of claim 9 wherein (b) is present in the composition in an amount of from about 5 to about 40% by weight, based on the weight of the composition.

14. The method of claim 9 wherein (d) is trimethyl pentaphenyl trisiloxane.

15. The method of claim 9 wherein (d) is present in the composition in an amount of from about 5 to about 50% by weight, based on the weight of the composition.

16. The method of claim 9 wherein the ratio by weight of (b) to (a) in the composition ranges from between about 1.5 to about 3.0.

17. The composition of claim 1, wherein (a) comprises trimethylsiloxysilacate, (b) comprises nylon-611/dimethicone copolymer and (d) comprises trimethyl pentaphenyl trisiloxane.

18. The composition of claim 17, wherein (a) is present in an amount of about %5 to about 30% by weight, (b) is present in an amount of about 15% to about 30% by weight, and (d) is present in an amount of from 15% to about 30% by weight, all weights being based on the total weight of the composition.

19. The composition of claim 18, wherein (c) comprises isododecane.

20. The composition of claim 19, wherein (c) is present in an amount of about 15% to about 25% by weight.

* * * * *

UNITED STATES PATENT AND TRADEMARK OFFICE
CERTIFICATE OF CORRECTION

| | | |
|---|---|---|
| PATENT NO. | : 8,945,525 B2 | Page 1 of 1 |
| APPLICATION NO. | : 12/981882 | |
| DATED | : February 3, 2015 | |
| INVENTOR(S) | : Kimberly Bradshaw et al. | |

It is certified that error appears in the above-identified patent and that said Letters Patent is hereby corrected as shown below:

In the claims,

Column 14, line 22, "%5" should read --5%--.

Signed and Sealed this
Twelfth Day of January, 2016

Michelle K. Lee
*Director of the United States Patent and Trademark Office*